United States Patent [19]

Stahl

[11] Patent Number: 5,432,260

[45] Date of Patent: Jul. 11, 1995

[54] HIGH AFFINITY MANNOSE RECEPTOR LIGANDS

[75] Inventor: Philip D. Stahl, Clayton, Mo.

[73] Assignee: Washington University, St. Louis, Mo.

[21] Appl. No.: 694,983

[22] Filed: May 3, 1991

[51] Int. Cl.⁶ .................... C07K 9/00; C07K 17/00; A61K 38/14; A61K 39/385
[52] U.S. Cl. .................. 530/322; 530/345; 530/377; 530/395; 530/402; 530/403; 436/518; 435/188; 424/193.1
[58] Field of Search .............. 530/322, 395, 329, 328, 530/327, 326, 345, 377, 403, 402; 514/773, 46, 2, 8, 29, 31, 34, 37, 39; 536/4.1; 424/184.1, 193.1; 436/518

[56] References Cited

U.S. PATENT DOCUMENTS 4,386,026 5/1983 Ponpipom et al. ............ 536/53
4,946,675 8/1990 Baldwin et al. ............... 514/23
5,028,594 7/1991 Carson ........................... 514/23

OTHER PUBLICATIONS

Crocker et al., *J. Exp. Med.* (1986) 164:1862–1875.
Aminoff et al., *Proc. Natl. Acad. Sci.* (1977) 74:1521–1524.
Schlepper-Schaffer et al., *Biochem. Biophys. Res. Commun.* (1983) 115:551–559.
De May et al., *Proc. Natl. Acad. Sci.* (1978) 75:1339–1343.
Lennartz et al., *J. Biol. Chem.* (1989) 264:2385–2390.
Lennartz et al., *J. Biol. Chem.* (1987) 262(21):9942–9944.
Taylor et al., *J. Biol. Chem.* (1990) 265(21):12156–12162.
Ezekowitz et al., *J. Cell. Sci.* (1988) Suppl. 9:121–133.
Stahl et al., *Cell* (1980) 19:207–215.
Ponpipom et al., *J. Med. Chem.* (1981) 24:1388–1395.
Wileman et al; PNAS (USA) 83:2501–2505 Apr. 7, 1986.
Westcott et al; *J. Biol. Chem.* 262(13):6101–6107 (1987).
Tong et al; *J. Biol. Chem.* 264(14):7962–7969 (May 15, 1989).
Dong et al; *J. Biol. Chem.* 265(8):4210–4217 (Mar. 15, 1990).
Chao et al; *EMBO J.* 9(11):3507–3513 (Nov. 1990).
Li et al; *J. Biol. Chem.* 266(26):17621–17630 (Sep. 15, 1991).
Taylor et al; *J. Biol. Chem.* 267(3):1719–1726 (Jan. 25, 1992).
Rogers et al; *J. Biol. Chem.* 265(17):9722–9727 (Jun. 15, 1990).
Doebber et al; *J. Biol. Chem.* 257(5):2193–2199 (Mar. 10, 1982).
Hoppe et al; *Biochemistry* 23:1723–1730 (1984).
MacDonald, et al., *J. Biol. Chem.* (1989) 264(6):3256–3261.

*Primary Examiner*—Kay K. A. Kim
*Attorney, Agent, or Firm*—Morrison & Foerster

[57] ABSTRACT

Polypeptide backbones containing sugar residues at repetitive intervals are capable of binding the mannose receptor when said sugars are mannosyl, fucosyl, or N-acetyl glucosamine residues. These peptides are of the formula $$X-(Z(Sa)AA_{n1})_{n2}-Y \qquad (1)$$

wherein Sa represents a mannose, fucose, glucose or N-acetylglucosamine residue optionally coupled to a linker moiety; Z is the residue of an amino acid to which S is coupled; each AA is independently the residue of an additional amino acid, n1 is an integer=1, 2 or 3; n2 is 3–15, and X and Y are noninterfering substituents. They are useful in the treatment of various diseases mediated by macrophage activity and proliferation.

21 Claims, 5 Drawing Sheets

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Lys  Gly  Gly  Lys
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Lys  Ser  Ser  Lys
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Lys  Gly  Ser  Lys
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Lys  Ser  Gly  Lys
    1

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Lys  Pro  Gly  Lys
    1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Lys  Pro  Gly  Gly
    1

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Lys  Pro  Gly  Gly  Lys
    1                      5

( 2 ) INFORMATION FOR SEQ ID NO:8:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

Lys Ala Ala Lys
1

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /label=Ac- ( i x ) FEATURE:
        ( A ) NAME/KEY: Peptide
        ( B ) LOCATION: 15
        ( D ) OTHER INFORMATION: /label=-NH2

( x i ) SEQUENCE DESCRIPTION: SEQ ID NO:9:

Tyr Lys Ser Lys Ser Lys Ser Lys Ser Lys Ser Lys Ser Lys Ser
1              5                      10                    15

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /label=Ac- ( i x ) FEATURE:
        ( A ) NAME/KEY: Peptide
        ( B ) LOCATION: 21
        ( D ) OTHER INFORMATION: /label=-NH2

( x i ) SEQUENCE DESCRIPTION: SEQ ID NO:10:

Tyr Lys Ser Lys Ser Lys Ser Lys Ser Lys Ser Lys Ser Lys Ser Lys
1            5                      10                    15

Ser Lys Ser Lys Ser
        20

( 2 ) INFORMATION FOR SEQ ID NO:11:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide (B) LOCATION: 1
(D) OTHER INFORMATION: /label=Ac- (ix) FEATURE:
(A) NAME/KEY: Peptide
(B) LOCATION: 14
(D) OTHER INFORMATION: /label=- NH2

(xi) SEQUENCE DESCRIPTION: SEQ ID NO:11:

Tyr Lys Gly Lys Gly Lys Gly Lys Gly Lys Gly Lys Gly Lys
1               5                           10

(2) INFORMATION FOR SEQ ID NO:12:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /label=Ac- (ix) FEATURE:
(A) NAME/KEY: Peptide
(B) LOCATION: 20
(D) OTHER INFORMATION: /label=- NH2

(xi) SEQUENCE DESCRIPTION: SEQ ID NO:12:

Tyr Lys Gly Lys Gly Lys Gly Lys Gly Lys Gly Lys Gly Lys Gly Lys
1               5                           10                          15
Gly Lys Gly Lys
            20

(2) INFORMATION FOR SEQ ID NO:13:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /label=Ac- (ix) FEATURE:
(A) NAME/KEY: Peptide
(B) LOCATION: 20
(D) OTHER INFORMATION: /label=- NH2

(xi) SEQUENCE DESCRIPTION: SEQ ID NO:13:

Tyr Lys Gly Gly Lys Gly Gly Lys Gly Gly Lys Gly Gly Lys Gly Gly
1               5                           10                          15
Lys Gly Gly Lys
            20

(2) INFORMATION FOR SEQ ID NO:14:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide ( i x ) FEATURE:
    ( A ) NAME/KEY: Peptide
    ( B ) LOCATION: 1
    ( D ) OTHER INFORMATION: /label=Ac- ( i x ) FEATURE:
    ( A ) NAME/KEY: Peptide
    ( B ) LOCATION: 29
    ( D ) OTHER INFORMATION: /label=-NH2

( x i ) SEQUENCE DESCRIPTION: SEQ ID NO:14:

Tyr Lys Gly Gly Lys Gly Gly Lys Gly Gly Lys Gly Gly Lys Gly Gly
1           5               10                  15

Lys Gly Gly Lys Gly Gly Lys Gly Gly Lys Gly Gly Lys
        20              25

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /label=Ac- ( i x ) FEATURE:
        ( A ) NAME/KEY: Peptide
        ( B ) LOCATION: 11
        ( D ) OTHER INFORMATION: /label=-NH2

( x i ) SEQUENCE DESCRIPTION: SEQ ID NO:15:

Tyr Lys Lys Lys Lys Lys Lys Lys Lys Lys Lys
1           5               10

( 2 ) INFORMATION FOR SEQ ID NO:16:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /label=Ac- ( i x ) FEATURE:
        ( A ) NAME/KEY: Peptide
        ( B ) LOCATION: 18
        ( D ) OTHER INFORMATION: /label=-NH2

( x i ) SEQUENCE DESCRIPTION: SEQ ID NO:16:

Tyr Lys Ser Lys Ser Lys Ser Lys Ser Lys Ser Lys Ser Lys Ser Lys
1           5               10                  15

Ser Lys ( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /label=Ac- ( i x ) FEATURE:
  ( A ) NAME/KEY: Peptide
  ( B ) LOCATION: 7
  ( D ) OTHER INFORMATION: /label=- NH2

( x i ) SEQUENCE DESCRIPTION: SEQ ID NO:17:

Tyr Lys Gly Lys Gly Lys Gly
1           5

( 2 ) INFORMATION FOR SEQ ID NO:18:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /label=Ac- ( i x ) FEATURE:
    ( A ) NAME/KEY: Peptide
    ( B ) LOCATION: 11
    ( D ) OTHER INFORMATION: /label=- NH2

( x i ) SEQUENCE DESCRIPTION: SEQ ID NO:18:

Tyr Lys Gly Lys Gly Lys Gly Lys Gly Lys Gly
1           5                   10

( 2 ) INFORMATION FOR SEQ ID NO:19:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /label=Ac- ( i x ) FEATURE:
    ( A ) NAME/KEY: Peptide
    ( B ) LOCATION: 15
    ( D ) OTHER INFORMATION: /label=- NH2

( x i ) SEQUENCE DESCRIPTION: SEQ ID NO:19:

Tyr Lys Gly Lys Gly Lys Gly Lys Gly Lys Gly Lys Gly Lys Gly
1           5                   10                  15

HIGH AFFINITY MANNOSE RECEPTOR LIGANDS

TECHNICAL FIELD

The invention relates to therapeutic and diagnostic reagents which specifically bind to receptors which recognize mannose residues. In particular, it concerns synthetic compounds that can target macrophage populations in animal subjects.

BACKGROUND AND RELATED ART

Macrophages are known to express, dependent on their state of development, several receptors which are specific for glycoproteins that contain specific sugars. These include receptors specific for sialic acid residues (Crocker, P., et al., *J Exp Med* (1986) 164:1862); receptors specific for galactose (Aminoff, D., et al., *Proc Natl Acad Sci USA* (1977) 74:1521; Schlepper-Schaffer, J., et al., *Biochem Biophys Res Comm* (1983) 115:551); and receptors specific for mannose residues (de May, et al., *Proc Natl Acad Sci USA* (1978) 75:1339). The mannose receptor is uniquely found on macrophages, and is not found on monocytes. The synthesis and processing of the macrophage receptor were described by Lennartz, M. R. et al., *J Biol Chem* (1989) 264:2385–2390.

The mannose receptor itself is a 170 kD glycoprotein which has been isolated from several sources. The human placental receptor has been characterized and the gene cloned and sequenced (Lennartz, M. R. et al., *J Biol Chem* (1987) 262:9942–9944; Taylor, M. E. et al., *J Biol Chem* (1990) 265:12156– 12162, the latter paper incorporated herein by reference).

A good deal is known about the behavior of the mannose receptor in internalizing ligands to which it binds. After internalizing the receptor ligand complex, the intracellular vesicles containing the complexes become acidic and dissociate the complex. The unoccupied receptor is returned to the cell surface while the ligand remains inside the cell. This cycle takes less than 15 minutes, and receptor molecules have half-lives of more than 30 hours, thus offering the capability to perform hundreds of cycles with respect to a single receptor. It has been shown that alveolar macrophages can accumulate about $50 \times 10^6$ molecules of mannose-BSA ligand per cell per 24 hours. (Ezekowitz, R. A. B., et al., *J Cell Sci* (1988) *Supp.* 9:121).

While mannose binding receptors regardless of source in general show similar specificities—i.e., recognize glycoproteins with terminal mannose and fucose and, to some extent N-acetylglucosamine and glucose, it appears that the quantitative affinity of these receptors for various ligands depends on their cellular origin. For example, N-acetylglucosamine-BSA (bovine serum albumin) binds reasonably well to alveolar macrophage but binds poorly to human placental mannose receptor. Adding further complexity is the presence of an approximately 30 kD mannose binding protein which is secreted by liver hepatocytes. The gene for this protein has also been cloned and sequenced (Ezekowitz, R. A. B. (supra)).

It is known that BSA or HSA (human serum albumin) derivatized to mannose through lysyl residues in the structure is a potent binder to the mannose ligand (Stahl, P. et al., *Cell* (1980) 19:207–215). Most BSA preparations contain about 57 lysines, of which 30–40 are coupled with mannose in a standard mannose-BSA preparation. In addition, one of the known native targets for the receptor, yeast mannan, is a polymannose ($\alpha$1-6) backbone with mono-, di- and trisaccharide sidechains linked $\alpha$1,2 and $\alpha$1,3 to the backbone. However, these materials are not ideal targeting agents for macrophage as they are inherently heterogeneous compositions and do not provide reproducible binding affinities satisfactory for pharmaceutical applications. It would therefore be helpful to have a defined composition as a high affinity ligand for the macrophage receptor.

Others have attempted to synthesize ligands containing mannosyl residues. For example, Ponpipom, M. M. et al., *J Med Chem* (1981) 24:1388–1395, describe mono-, di- and oligolysine backbones which are derivatized to mannosyl or fucosyl residues through short covalent linking arms. In addition, this paper reports polymerization of N-lipoyl-$\beta$-D-mannopyranosylamine to result in an effective receptor binding ligand. The best of these was able to effect 50% inhibition of labeled mannosylated BSA binding to macrophage only at concentrations greater than 10 $\mu$M.

DISCLOSURE OF THE INVENTION

The invention provides defined polypeptide backbones for derivatization to mannosyl or other sugar residues which compositions can be used to target the mannose receptor on macrophage specifically and which enhances the repertoire of available ligands for receptor binding. The definitive character of the backbone further provides the opportunity to design structures which preferentially bind macrophage receptor protein in particular cell types, and with respect to which the effect of circulating mannose binding protein can be minimized, as well as to provide optimal spacing of the sugar residues to result in higher affinities than those presently available in homogeneous carriers. These materials can readily be prepared in homogeneous form and used in the synthesis of suitable pharmaceuticals and diagnostics.

Accordingly, in one aspect, the invention is directed to a synthetic polypeptide scaffold containing at regular intervals thereon at least three mannose, fucose, glucose or N-acetyl glucosamine residues or mixtures thereof covalently bonded to the polypeptide backbone through the 1-position of these sugar residues. In general, typical carrier ligands of the invention have the formula

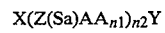    (1)

wherein Z is an amino acid residue to which a mannose, fucose, glucose or N-acetyl glucosamine substituent (Sa) is coupled generally through a linking arm, each AA is independently a spacer amino acid residue, n1 is 1, 2, or 3, and when n1 is 2 or 3 each AA need not be the same as the others, n2 is an integer of 3–15, and X and Y are the N- and C-termini or can be noninterfering substituents, such as additional peptide extensions or linker moieties. In preferred forms of the synthetic mannose receptor targeting ligands of the invention, the polypeptide backbone is a standard repeating unit which contains a lysyl residue as Z for covalent bonding of the saccharide. The compounds of the invention further may contain additional amino acids or other linking residues to provide a means to couple additional moieties for internalization into macrophage when this is desired or which have other functions such as labeling or cytotoxicity.

In additional aspects, the invention is directed to pharmaceutical compositions containing the high affinity mannose receptor ligand of the invention coupled to an effector moiety, and to methods of treatment for asthma, inflammatory diseases, and infectious diseases utilizing these pharmaceutical compositions.

MODES OF CARRYING OUT THE INVENTION

Figure 1:
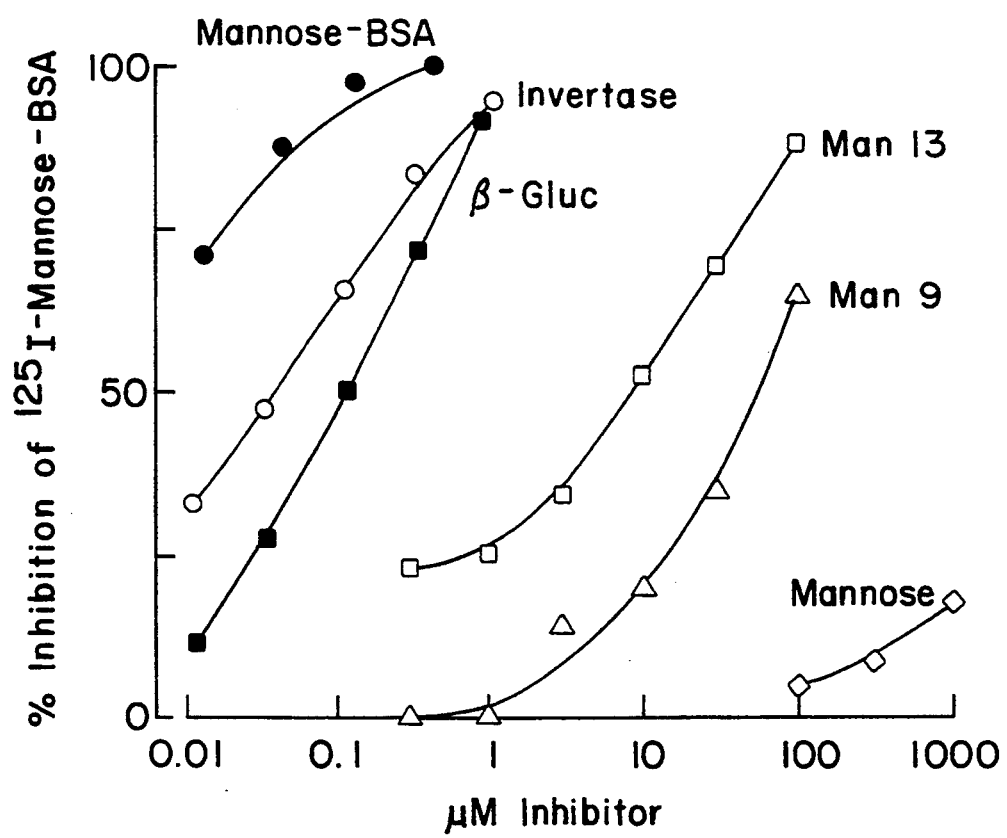
FIG. 1 is a graphical representation of the ability of polysaccharides and naturally occurring proteins to inhibit the binding of mannose-labeled BSA to purified mannose receptor.

The invention high affinity mannose receptor binding ligands are repetitive synthetic polypeptides which contain coupled sugar residues at regular intervals. The sugar residues are those that mediate binding to the mannose receptor and include glucose, fucose, N-acetyl glucosamine, and mannose; in general, mannose residues are preferred. As used herein, "regular intervals" refers to close repetitive spacing of the sugar residues along the polypeptide chain—i.e., the sugars are derivatized to amino acid residues which are separated by one, two, or three intervening amino acid residues wherein a specific pattern is repeated. This structure is intended to mimic an extended mannan-like oligosaccharide, rather than a typical N-linked triantennary mannose-oligosaccharide. Thus, examples of regular spacing include those wherein, for example, a series of five sugar residues are bound through the sidechain nitrogens of lysine residues in a backbone where each lysine is separated from the succeeding lysine by one amino acid residue; an additional example would provide a backbone which includes the foregoing series of five lysine residues, each separated by two amino acids. Not excluded, however, from "regular intervals" are occasional deviations from exactly perfect repetition or alternative regularities such as alternate spacings of 2/1/2/1, etc. In addition, all sugar residues may be the same, or two or more different sugars may be coupled to the backbone.

As indicated above, one convenient method for covalently linking sugar residues to polypeptide backbones is through the sidechain amino groups of lysine residues in the amino acid sequence. As the peptide sequences are synthetic, there is no need to include only gene-encoded amino acids; alternative residues such as γ-aminobutyric acid or other amino acids containing amino groups in the sidechains could also be used. If desired, by altering the preparation method, the side chain hydroxyl groups of, for example, serine or threonine could also be used. Since standard synthetic peptide techniques can be employed to prepare the peptide backbones, amino acid residues containing functional groups which provide linking moieties for conjugation of additional ligands, such as labels, cytotoxic moieties, cofactors, or other effector substituents, can be included in the amino acid sequence. The amino acid sequence itself may further be extended to contain peptides of physiological significance, such as various stimulating or inhibiting factors, or larger proteins which have been recombinantly produced or isolated from native sources can be enzymatically attached to the peptide chain. These may be prepared as fusion proteins or coupled using alternative chemical techniques. A significant number of homobifunctional and heterobifunctional linkers are also commercially available which permit conjugation of a variety of moieties to the peptide backbone.

Synthesis of the Sugar-Containing Ligands

Multiple sugar residues can be conjugated to the polypeptide backbone containing residues with amino groups in their sidechains by the method of Lee, Y. C., et al., *Biochemistry* (1976) 15:3956. Briefly, peracetylated cyanomethylthiomannose or the corresponding derivative of glucose, fucose or N-acetyl glucosamine (GlcNAc) is used as the starting material. These are commercially available or can be synthesized as described in this reference. The thioglycoside is converted to the 2-imino-2-methoxyethyl-1-thioglycoside by treatment with sodium methoxide in dry methanol which simultaneously deacetylates the sugar; the 1-position of the glycoside residue thus bears the functional group $-SCH_2C(NH)OMe$. This material reacts directly with the sidechain amino residues in aqueous medium at a pH of about 3.5 by displacement of the methoxy residue by the amino nitrogen to obtain the $-SCH_2C(NH)NH$ linkage. The products can then be purified by reverse phase HPLC. Additional methods to effect linkage of the sugars to sidechain amino or hydroxyl groups, such as those set forth in Ponpipom, M. M. et al. (supra) can also be used.

Any polypeptides that are only partially derivatized can be removed by reaction with ninhydrin which is preferentially reactive with the primary amines on unreactive sidechains. The partially derivatized polypeptides can also be separated from fully derivatized polypeptides using gel or paper electrophoresis.

For substances containing five sugar residues or less, partial derivatization does not appear to be a problem; however, the accumulation of positive charges at pH values needed for the reaction due to the presence of multiple amidine groups appears to cause problems in allowing the reaction to go to completion. However, peptide chains with larger numbers of glycoside residues can be built from subunits containing five or less sugar residues by coupling of the components, for example through reduction of two cysteine-derivatized molecules.

Alternatively, the sugar residues can be derivatized to the peptide chain using a benzoyl ether linking arm (which does not result in a positive charge).

In this approach, the sugar residue is fully acetylated and then reacted with methyl p-hydroxybenzoate in the presence of an acid catalyst. The resulting acetylated p-glycosyl benzoate is saponified in lithium hydroxide/methanol/water to obtain the free acid, which is then converted to the carboxylic azide by treatment with $(Ph)_2PON_3$ in the presence of either dimethylformamide and triethylamine or dicyclohexylcarbodiimide. The carboxyl azide then is directly reacted with the amino groups in the polypeptide sidechains to obtain the amide and the acetyl protecting groups are removed by treatment with barium hydroxide in methanol. In the alternative, the intermediate acetylated p-glycosyl benzoic acid is deprotected, and then conjugated to the peptide with disuccinylcarbonate (DSC).

In addition, mannosyl or other glycosyl sidechains are extendable by enzymatic catalysis using suitable enzymes (Lehrman, M. A., et al., *J Biol Chem* (1986) 261:7412).

As noted above, the "mannose" receptor also recognizes terminal fucose, glucose, and N-acetyl glucosamine residues. Thus, the glycose residues in the compounds of formula (1) can be independently selected from these. The choice of such sugar residues is significant in determining binding affinity of the ligand. The mannose receptors on macrophages of various origins differ in specificity profiles, and specific macrophage populations can thus be preferentially targeted by adjusting the mannose/fucose/glucose/N-acetyl glucosamine content of the peptides. Polypeptides with mixed saccharide residues at regular intervals can be prepared either obtaining random distribution by using mixtures of saccharides in the glycosylation reactions or in regular patterns by splicing peptide segments containing substitutions of only one residue prepared as outlined above.

PREFERRED EMBODIMENTS

Exemplary embodiments of the invention compositions include those of formula (1) which are:

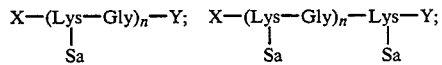

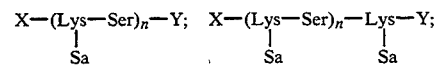

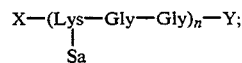

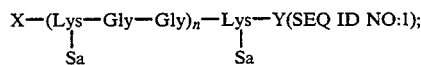

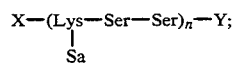

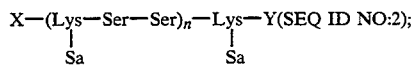

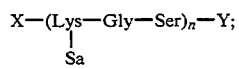

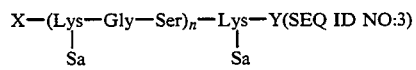

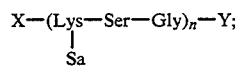

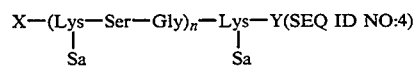

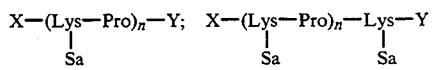

-continued

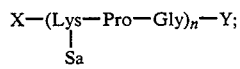

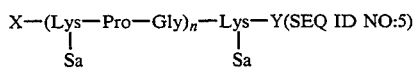

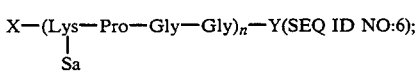

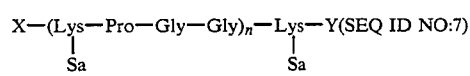

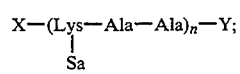

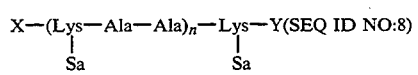

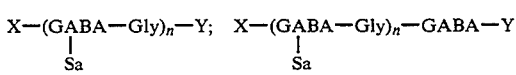

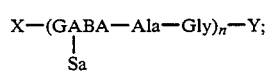

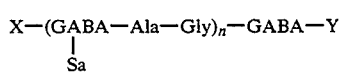

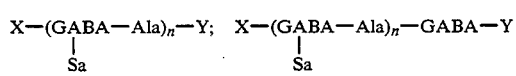

wherein n is 3–15 and wherein X and Y are independently the N-terminal and C-terminal H or OH, or the acylated and/or amidated forms or are additional amino acid residues (including their acylated and/or amidated forms) or linking groups. Preferred "n" is 4–10. Typical embodiments for X or Y, include, for example, tyrosyl residues, to which can be conveniently bound an iodide for labeling; an aspartyl or glutamyl residue which provides a carboxyl group for conjugation to additional moieties; linking groups such as the homo- and heterobifunctional linkers marketed by Pierce Chemical Company, Rockford, Ill., or additional Gly, Ala, Ser, Pro or other amino acid residues which merely extend the peptide chain. In particularly preferred embodiments of the formulas above, X is acetyl tyrosine and Y is NH$_2$.

All of the compounds shown, at the Lys or GABA residues, contain a suitable saccharide unit linked through the ω-amino group generally through a covalent linking arm. Preferred embodiments of the saccharide are the 1'-mannose residues designed to confer binding of the composition to the mannose receptor. However, as stated above, it is also known that fucose, glucose and N-acetylglucosamine residues bind to greater or lesser extent to these receptors depending on the source of the macrophage. Preferred linking arms include

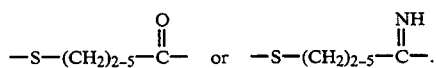

The embodiments of "S" can be identical in all of the monomers shown in the formulas above, or can be different.

Particularly preferred are
Ac-Tyr-(Lys-Ser)$_7$—NH$_2$ (SEQ ID NO: 9);
Ac-Tyr-(Lys-Ser)$_{10}$—NH$_2$ (SEQ ID NO: 10);
Ac-Tyr-(Lys-Gly)$_6$-Lys—NH$_2$ (SEQ ID NO: 11);
Ac-Tyr-(Lys-Gly)$_9$-Lys—NH$_2$ (SEQ ID NO: 12);
Ac-Tyr-(Lys-Gly-Gly)$_6$-Lys—NH$_2$ (SEQ ID NO: 13); and
Ac-Tyr-(Lys-Gly-Gly)$_9$-Lys—NH$_2$ (SEQ ID NO: 14), containing mannosyl residues linked to the lysine residues through the —S(CH$_2$)$_2$CO— or —S(CH$_2$)$_2$CNH— linking arms.

ASSAYS

All of the compositions of the invention are capable of binding to the mannose receptor on macrophage and thus must meet this criterion as judged by a suitable assay. The compounds are considered effective in binding the mannose receptor if they exhibit an IC$_{50}$ of 1 μM or less in the competition assay conducted as follows:

The assay measures the ability of the test compound to inhibit the binding of $^{125}$I-mannose-BSA, prepared as described, to isolated mannose receptor. To prepare solid supported receptor protein A-sepharose (IgG-SORB) is incubated with rabbit anti-human mannose receptor antiserum for 20 minutes at room temperature. The beads are then washed by sedimentation 3 times in Tris-buffered saline containing 1% Triton X-100, 1% BSA and 15 mM CaCl$_2$ (assay buffer). The beads are then suspended in an assay buffer and purified mannose receptor (Lennartz, M. R. et al., *J Biol Chem* (1987) 262:9942–9944 (supra)) is added, followed by incubation for 30 minutes at 37° C. The beads are washed again three times to remove unbound receptor.

In the assay, the receptor-linked beads are resuspended in a total volume of 100 μL assay buffer containing 0.1 μCi $^{125}$I-mannose-BSA (2 nM) prepared according to (Stahl, P. et al., *Cell* (1980) (supra)) with and without test compound. Following incubation at 37° C. for 15 minutes, the beads are diluted in ice cold buffer and washed three times in the same assay buffer as the dissociation or receptor/ligand at 4° C. is quite slow. The cpm of $^{125}$I-mannose-BSA remaining in the buffer is determined, and the percent inhibition of test compound at various concentrations calculated. The IC$_{50}$ is then the concentration which effects a 50% inhibition in binding. Nonspecific binding of ligand to beads is determined by adding excess yeast mannan to parallel assays and accounted for in the calculations.

The $^{125}$I-mannose-BSA used in the assay binds to receptor beads with a K$_d$ of 2 nM as determined in the foregoing assay using unlabeled mannose-BSA as test compound.

ADMINISTRATION AND USE

The compositions of the invention provide a mechanism to target macrophages specifically to the exclusion of other cells and thus provide means to label or image macrophages, to destroy macrophages, or to otherwise alter or modify the metabolism, evidenced as antigen processing function, of macrophages specifically. Thus, the compositions of the invention are typically administered coupled to moieties designed to provide the effector function such as those set forth above. In addition, the ligands of the invention can be conjugated to solid supports and used to purify mannose receptors from a variety of sources.

Typical labeling compounds include radioisotopes such as $^{125}$I, $^{32}$P, isotopes which emit sufficient radiation to be counted by scintigraphic means in vivo, such as indium 111 or technetium 99 or other radioisotopes conventionally used. Other labels include enzymatic labels such as horseradish peroxidase or alkaline phosphatase which are conventionally used to label specific binding partners in specific binding assays, such as immunoassays. The enzymatic labeling of the compositions of the invention is particularly useful in instances wherein the ligands are used in in vitro assays, for example, for anti-ligand antibodies or for the ligand itself in competition assays. Chromophoric and fluorescent labels may also be used. These conjugates are useful for imaging the reticuloendothelial system in tumors or organs.

Typical effector units which affect the metabolism of the macrophage include cytotoxic materials such as ricin A chain, diphtheria toxin and the like; various drugs, such as methotrexate (MTX), dexamethasone, azidothymidine (AZT), and muramyl dipeptide; nutrients such as enzyme cofactors and other vitamins; and the like. Also included as effector units are antibiotics. In addition, the compositions of the invention may be conjugated to carriers as described in the section concerning preparation of antibodies or may be conjugated to solid supports for use in affinity preparation of receptors.

Depending on the form in which the compositions of the invention are administered, they are useful in a variety of indications. For example, when conjugated to moieties which destroy macrophage activity, the compositions are useful in the treatment of inflammatory diseases that are driven by macrophage secretory products such as Crohn's disease, infectious disease where macrophages harbor replicating infectious agents, such as Legionnaire's disease; viral infections that involve mononuclear phagocytes such as HIV, and lysosomal storage diseases where macrophages are the principal cell involved, for example, Gaucher's disease. These compositions are also useful in the treatment of asthma which is mediated by alveolar macrophages and in controlling metastasis which is mediated by systemic macrophages.

In addition, antigen peptides can be used as the effector moiety wherein these peptides are delivered more efficiently to macrophage to marshall an immune response. The ligands are thus useful as hapten carriers in vaccines. Self peptides may also be delivered to macrophage, resulting in prevention of tissue transplant rejection.

For administration of the compositions of the invention, suitable formulations to provide systemic delivery are used. Typically, such formulations include formulations for injection, such as Hank's solution, Ringer's solution or physiological saline or slow release systems or oral compositions, as is understood in the art. Compositions designed for transdermal or transmembrane delivery, such as aerosols or suppositories, can also be used. Suitable formulations can be found, for example, in *Remington's Pharmaceutical Sciences*, latest edition, Mack Publishing Company, Easton, Pa.

PREPARATION OF ANTIBODIES

The invention compositions can be used in standard immunization protocols to produce antibodies which are useful, for instance, in monitoring the therapeutic protocols using the compositions of the invention. Typical immunization protocols include repeated injection of the invention composition either alone or conjugated with carrier to mammalian subjects such as rabbits, mice, rats, sheep and the like. Immunization is monitored by assaying serum titers using standard immunoassay techniques with the invention composition as antigen. When suitable titers are obtained, the polyclonal antisera can be used in immunoassays or as an immunogen to produce antiidiotypes or monoclonal antibodies can be produced for these purposes. To produce the monoclonal preparations, peripheral blood lymphocytes or the spleens of the immunized animals are used as a source of antibody-secreting cells and immortalized by, for example, fusion to myelomas. The immortalized cells are screened using standard immunoassays for secretion of the appropriate antibodies. Other means for immortalizing the antibody producing cells, such as by viral infection, can also be used.

The following examples are intended to illustrate but not to limit the invention.

EXAMPLE 1

Inhibition of Receptor Binding by Glycosylated Protein

The competition was conducted as set forth above, using as test compounds, mannose, oligosaccharides containing 3, 5, 7, 9 or 13 mannose residues linked $\alpha 1, 4$ (Man$_9$ and Man$_{13}$, respectively) and two proteins known to contain mannose residues, $\beta$-glucuronidase and invertase. $^{125}$I-mannose-BSA at 2 nM was used in the assay and mannose-BSA was used in a control. Varying concentrations of test compound were used to determine the IC$_{50}$ for each material.

The results are shown in FIG. 1. As shown, IC$_{50}$ for Man$_9$ was approximately 20 $\mu$M; that for Man$_{13}$ was approximately 10 $\mu$M. Mannose itself was at least 1,000-fold less effective. Mannose-BSA itself shows an IC$_{50}$ less than 0.01 $\mu$M.

Invertase and $\beta$-glucuronidase both showed IC$_{50}$ in the range of 0.01–0.1 $\mu$M. $\beta$-glucuronidase is a tetramer having two high-mannose content chains per subunit. When $\beta$-glucuronidase and invertase were digested with pronase, their ability to inhibit the binding of $^{125}$I-mannosyl-BSA was destroyed. These results indicated that multivalent interactions accounted for the high affinity binding of these proteins.

EXAMPLE 2

Preparation of Glycosylated Peptides

The glycopeptides were synthesized in four steps. First, the unmannosylated peptides were made on an ABI peptide synthesizer. The peptides were then purified using reverse-phase and ion-exchange chromatography. Mannose units were then attached via a 2-imino-2-methoxyethyl thiomannopyranoside (Lee, Y. C., Biochemistry (1976) 15:3956). Finally, the mannosylated peptides were purified by reverse-phase and ion-exchange chromatography.

The acetylated and amidated peptides
Ac-Tyr-(Lys-Ser)$_7$—NH$_2$ (SEQ ID NO: 9);
Ac-Tyr-(Lys-Ser)$_{10}$—NH$_2$ (SEQ ID NO: 10);
Ac-Tyr-(Lys-Gly)$_6$-Lys—NH$_2$ (SEQ ID NO: 11);
Ac-Tyr-(Lys-Gly)$_9$-Lys—NH$_2$ (SEQ ID NO: 12);
Ac-Tyr-(Lys-Gly-Gly)$_6$-Lys—NH$_2$ (SEQ ID NO: 13);
Ac-Tyr-(Lys-Gly-Gly)$_9$-Lys—NH$_2$ (SEQ ID NO: 14) and
Ac-Tyr-(Lys)$_{10}$—NH$_2$ (SEQ ID NO: 15)

were synthesized by the Merrifield method on an Applied Biosystems Model 430A peptide synthesizer using p-methylbenzhydrylamine resin (Matusueda and Stewart, Peptides (1981) 2:45–50). tert-Butoxycarbonyl-amino-acids were converted to symmetrical anhydrides using dicyclohexylcarbodiimide. N-terminal acetylation was achieved by adding acetic anhydride, dimethylformamide, and pyridine in a ratio of (8:1:1, v/v/v) followed by washing with dimethylformamide and methylene chloride. The peptides were cleaved from the resin and deprotected using liquid hydrogen fluoride/anisole (9:1, v/v) for 60 min at 0° C. Free peptide was extracted from the resin with 33% acetic acid, filtered, and lyophilized.

A Synchropak CM-300 carboxymethyl weak cation exchanger was used on a Pharmacia FPLC system to isolate the complete peptides. The peptides were eluted using an ammonium acetate gradient, and desalted on an RP-HPLC system (LKB 2150). The purified peptides were then analyzed by amino acid analysis and mass spectrometry.

Ac-Tyr-(Lys-Ser)$_{10}$—NH$_2$ (SEQ ID NO: 10) could not be completely separated from the Ac-Tyr-(Lys-Ser)$_8$-Lys—NH$_2$ (SEQ ID NO: 16) incomplete form of the peptide without significant loss. It was therefore mannosylated with the complete peptide and separated out after mannosylation.

Mannose residues were covalently attached to the primary amines on the lysines by using a 2-imino-2-methoxyethyl thiomannopyranoside (IME). This linkage forms an amidino derivative which stimulates the cationic properties of the original amino group, thereby minimizing any tertiary structural change. The precursor to the IME was an acetylated cyanomethyl thiomannopyranoside (CNM, purchased from EY Labs). The intermediate IME was formed by reacting 100 mg CNM in 2.5 ml dry MeOH with 0.01M NaOMe generated in situ with dry sodium. The reaction mixture was incubated at room temperature for 48 hrs. Excess methanol was evaporated off by speed vac centrifugation. The oily pellet was then brought up in 1 ml of 0.1M disodium tetraborate buffer pH 9.3 containing 2 mg of peptide. The mannosylation was allowed to incubate at room temperature for 24 hrs before injection onto HPLC.

The coupling mixture was injected onto a Beckman ODS C18 reverse phase HPLC column. The mannosylated peptides eluted at approximately the same percent acetonitrile as the original peptides (within 1 minute retention). The collected peaks were then injected onto a Synchropak CM300 cation exchanger and eluted with an ammonium acetate gradient pH 8.0. The ion exchange resin separated the fully mannosylated peptides from any partial products based on the charge difference between primary and secondary amines (unmannosylated peptides had longer retention than their mannosylated counterparts). Finally, the major peak from the ion exchange run was collected and desalted over the reverse phase column. Identification and characterization of the glycopeptides was through amino acid analysis, mass spectrometry, Dionex carbohydrate chromatography system, and fluorescamine analysis for free amines to verify structure.

EXAMPLE 3

Binding of Invention Compositions to Receptor

Figure 2:
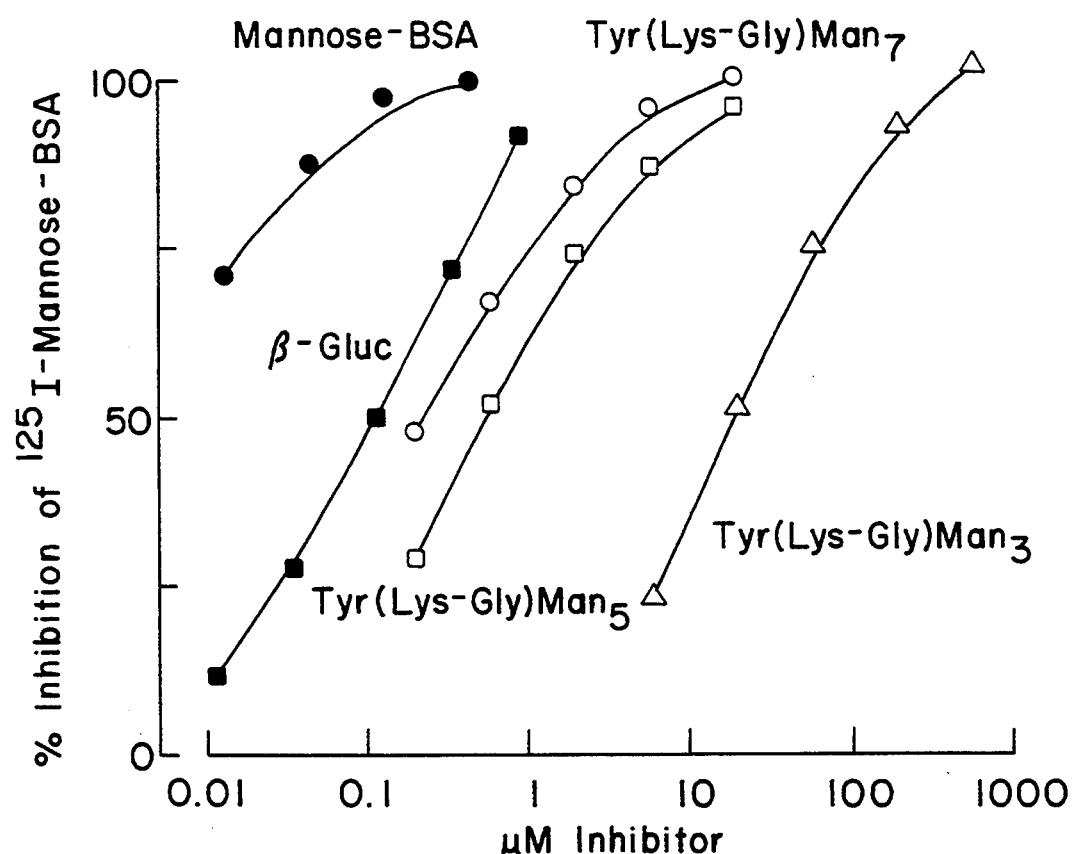
FIG. 2 is a graphical representation of the results of an assay determining the ability of the invention compositions to inhibit binding of labeled mannose to purified mannose receptor.
Figure 3:
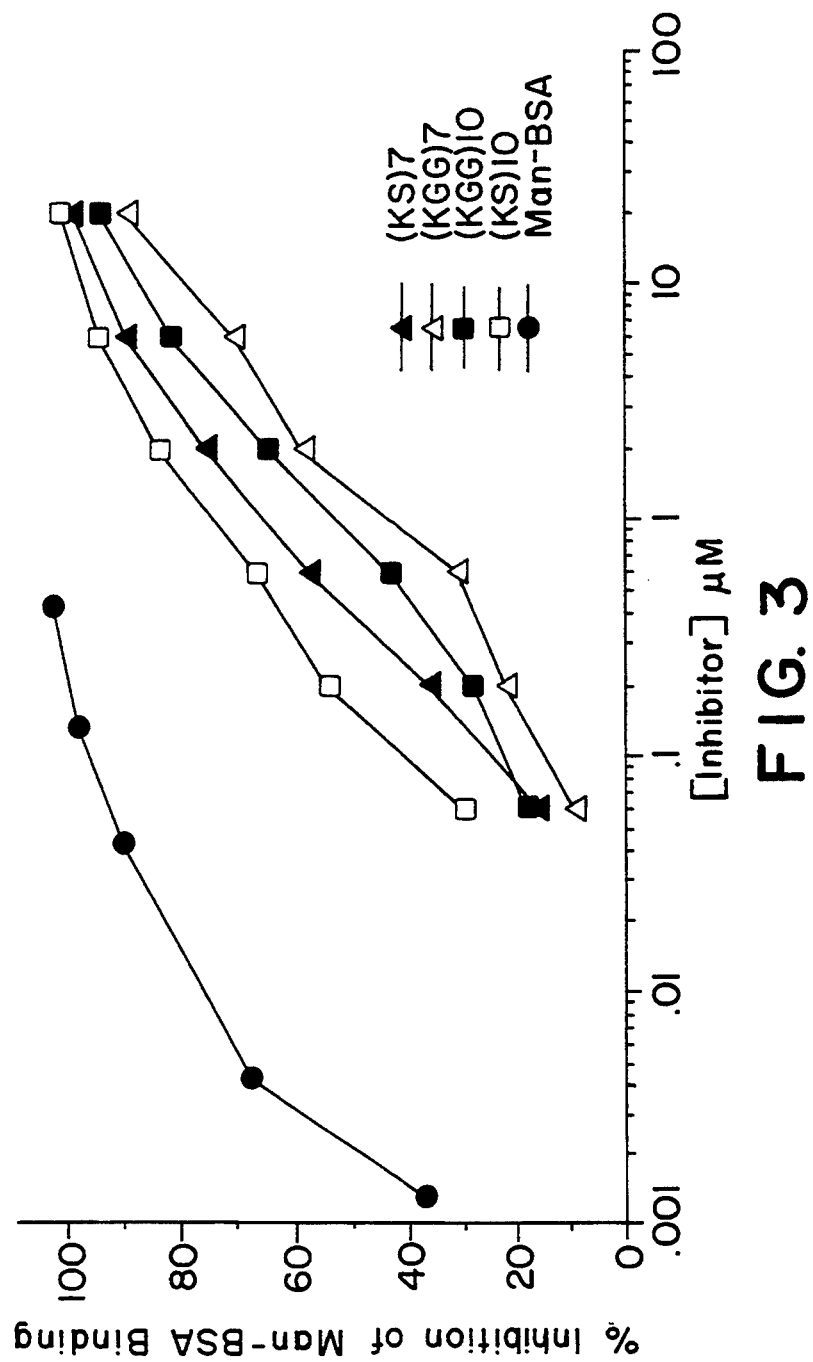
FIG. 3 shows the results of testing of additional compounds of the invention in the assay represented in FIG. 2.

The compounds synthesized in Example 2 were tested in the assay system described in Example 1 above under the conditions therein set forth. FIGS. 2 and 3 show the results. The $IC_{50}$ (concentration of test compound which effects 50% inhibition of binding of labeled mannose-BSA under the conditions of the assay) can be read from the figures.

As shown in FIG. 2, the $IC_{50}$ of test compound is enhanced as the number of mannosyl residues is increased over the range of 3–7. The $IC_{50}$ for $$\text{Ac—Tyr—(Lys—Gly)}_3\text{—NH}_2 \text{(SEQ ID NO:17)}$$
$$|$$
$$\text{Man}$$

is approximately 10 µM; for $$\text{Ac—Tyr—(Lys—Gly)}_5\text{—NH}_2 \text{(SEQ ID NO:18)},$$
$$|$$
$$\text{Man}$$

approximately 0.5 µM and for $$\text{Ac—Tyr—(Lys—Gly)}_7\text{—NH}_2 \text{(SEQ ID NO:19)},$$
$$|$$
$$\text{Man}$$

approximately 0.1 µM.

FIG. 3 shows $IC_{50}$ values for the series of test compounds of Example 2, all in the range of 0.1–1 µM.

EXAMPLE 4

Macrophage Uptake of Invention Compositions

The macrophages of cell line J774E (Diment, S. et al., *J Biol Chem* (1989) 264:13403–13406) were suspended in Hank's Balanced Salt Solution at $5 \times 10^5$ cells/100 ml. The suspension contained 1% BSA and 2 nM final concentration $^{125}$I-mannose-BSA prepared as described above. Incubation buffer containing the cells, as described above (100 µl) was suspended over 150 µl silicon oil in a microfuge tube, and the cells were incubated with or without test compound at 37° C. before they were spun through the oil and counted. Inhibition of $^{125}$I-mannose-BSA uptake by the test compound was corrected for nonspecific uptake, as determined by including 2 mg/ml yeast mannan in a control assay. Nonspecific uptake was generally less than 15%.

Figure 4:
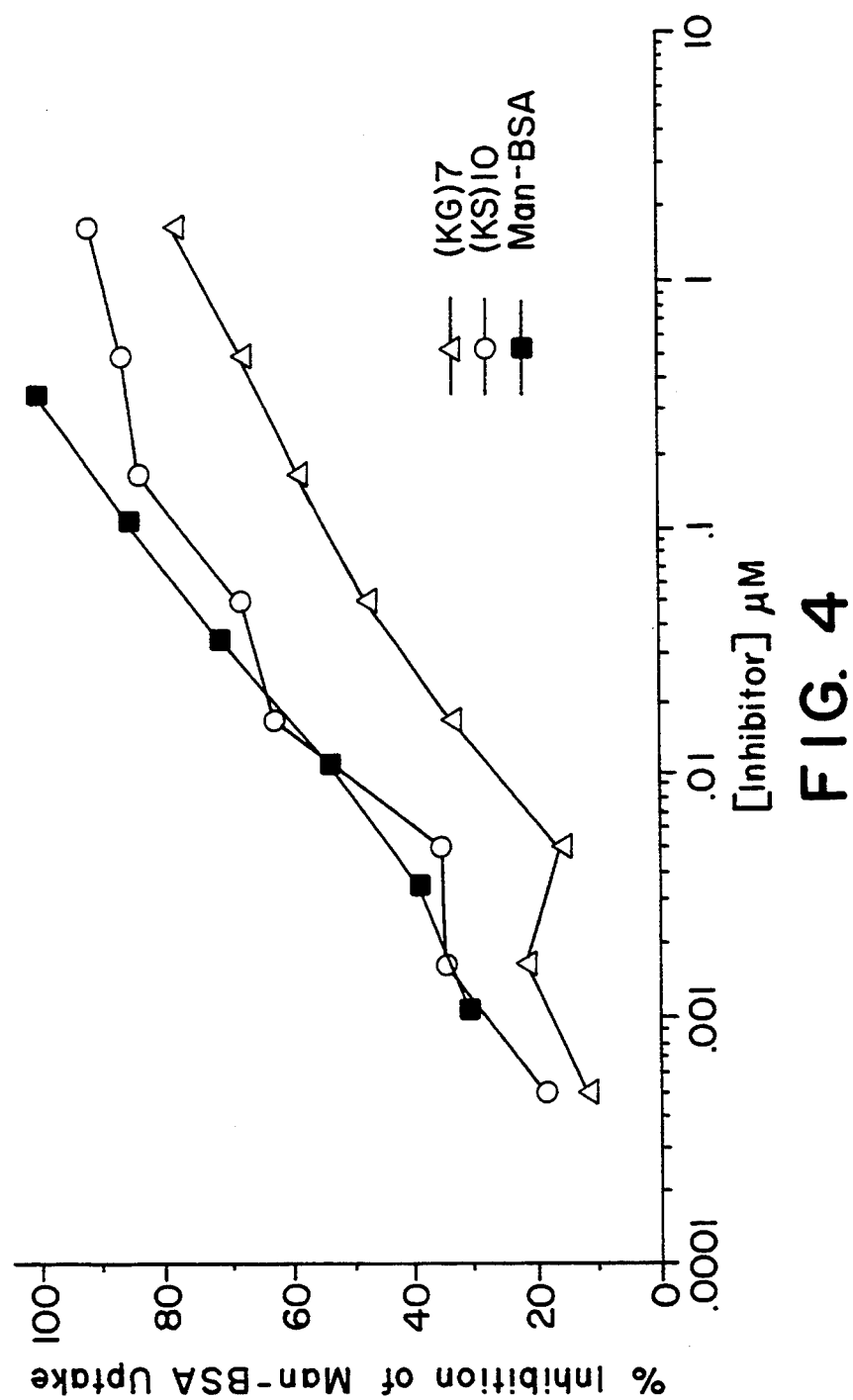
FIG. 4 shows the ability of the invention compounds to inhibit the uptake of labeled mannose BSA by J774 macrophage.
Figure 5:
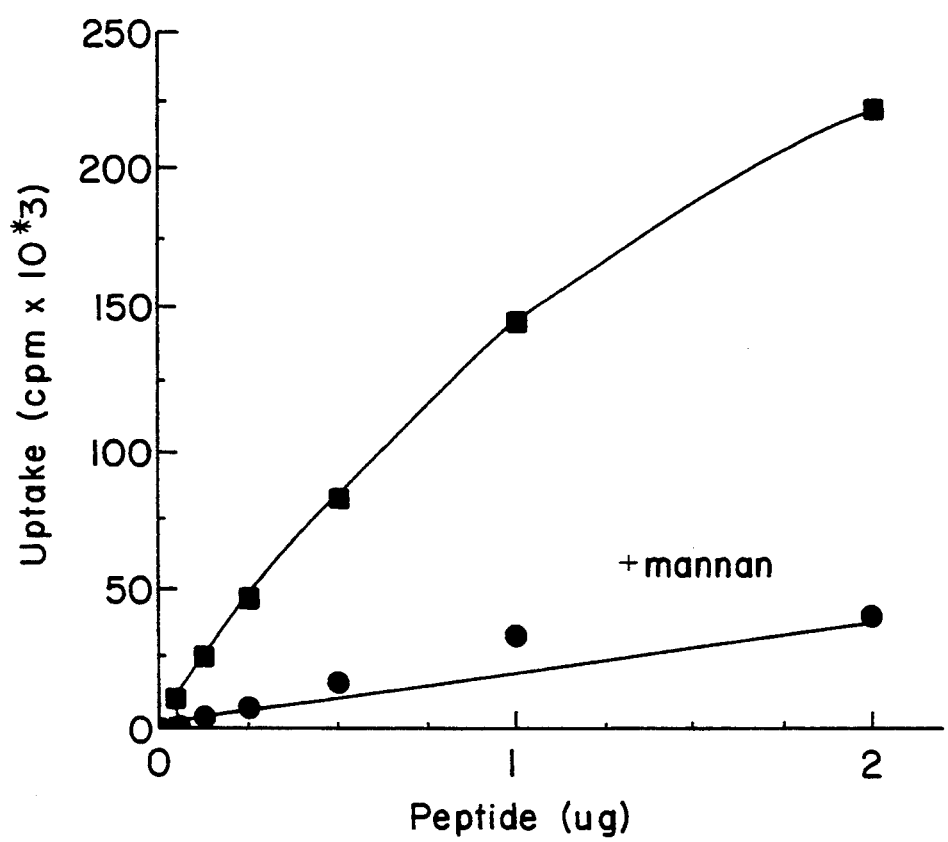
FIG. 5 shows the ability of (KManS)$_{10}$ labeled with $^{125}$I to be internalized by macrophage.

The results of one of these assays are shown in FIG. 4. Again, an $IC_{50}$ value can be calculated as the concentration of test compound, which causes 50% inhibition of the mannose-BSA uptake. Unlabeled mannose-BSA, itself, in this assay, has an $IC_{50}$ of approximately 0.004 µM. 
$$\text{Ac—Tyr(Lys—Ser)}_{10}\text{NH}_2 \text{(SEQ ID NO:10)}$$
$$|$$
$$\text{Man}$$

shows a similar $IC_{50}$, and $$\text{Ac—Tyr(Lys—Gly)}_7\text{—NH}_2 \text{(SEQ ID NO:10)}$$
$$|$$
$$\text{Man}$$

shows an $IC_{50}$ of approximately 0.02 µM. In an additional determination, $$\text{Ac—Tyr(Lys—Ser)}_{10}\text{NH}_2 \text{(SEQ ID NO:10)}$$
$$|$$
$$\text{Man}$$

was iodinated at the tyrosyl residue and incubated with J774E cells in the manner described above. The cells were incubated with labeled material for 30 minutes at 37° C. with increasing amounts of test compound, with or without yeast mannan, prior to being spun through the oil and counted. These results are shown in FIG. 5. The data show that there is a steady increase in the uptake of test compound as its concentration is increased over the range of 1–2 µg/100 µl.

---

I claim:
1. A mannose receptor binding compound of the formula

$$X-(Z(Sa)AA_{n1})_{n2}-Y \qquad (1)$$

wherein
Sa represents a mannose, fucose, glucose or N-acetylglucosamine linked through the C-1 carbon thereof to Z;
Z is an amino acid; each AA is independently an amino acid, all n1 are the same and n1 is an integer=1, 2 or 3;
n2 is an integer of 3–15, and X and Y are substituents which do not interfere with the binding of the compound of formula (1) to the mannose receptor.

2. The compound of claim 1 wherein Z is lysine or γ-aminobutyric acid.

3. The compound of claim 1 wherein n1 is 1 or 2 and n2 is 5–10.

4. A compound which has a formula selected from the group consisting of:

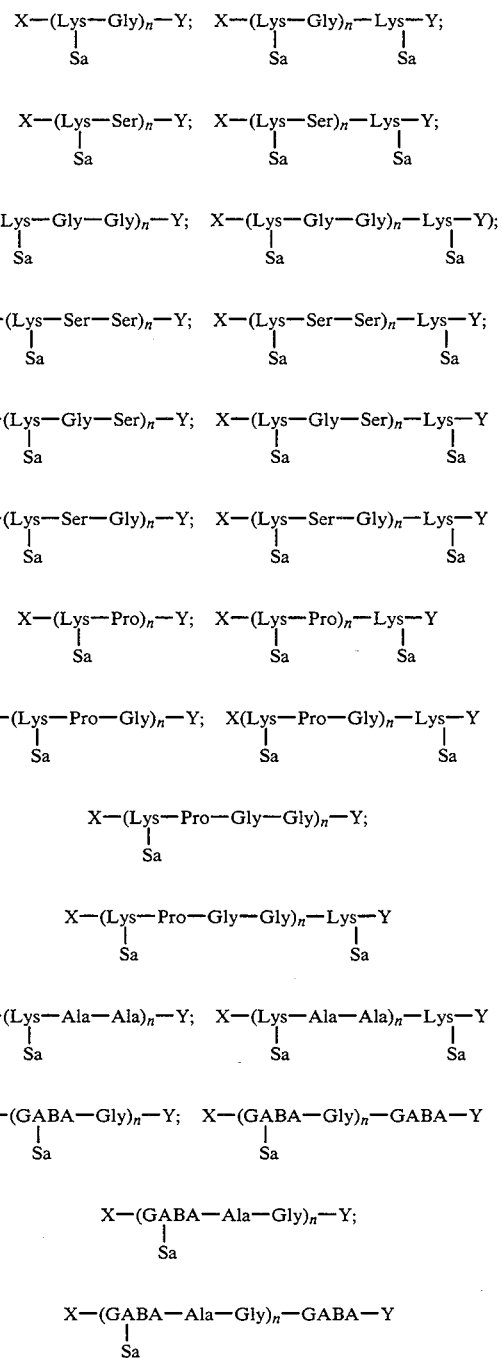

X—(GABA—Ala)$_n$—Y;   X—(GABA—Ala)$_n$—GABA—Y
　　　|　　　　　　　　　　　　　|
　　　Sa　　　　　　　　　　　　Sa wherein
X and Y are substituents which do not interfere with the binding of said compound to the mannose receptor,
each Sa is independently a mannose or fucose linked through its C-1 carbon to the lysine or GABA residue, and
n is an integer of 3–15.

5. The compound of claim 4 wherein each Sa is mannose.

6. The compound of claim 4 wherein n is 5–9.

7. A complex for drug delivery to cells having mannose receptors, which complex consists essentially of the compound of claim 1 covalently bonded to said drug to be delivered.

8. The complex of claim 7 wherein said drug is an antitumor agent.

9. The complex of claim 8 wherein said antitumor agent is methotrexate or azidothymidine.

10. The complex of claim 7 wherein said drug is an agent for imaging the reticuloendothelial system.

11. The complex of claim 7 wherein said drug is an antigenic peptide.

12. The complex of claim 7 wherein said drug is an antibiotic.

13. The complex of claim 7 wherein said drug is a toxin.

14. The complex of claim 13 wherein said toxin is ricin A chain or diphtheria toxin.

15. The compound of claim 4 wherein each Sa is mannose or fucose linked through its C-1 carbon to the lysine or GABA residue through a —S—(CH$_2$)$_{2-5}$—CO— or —S—(CH$_2$)$_{2-5}$—CNH— linking arm.

16. The compound of claim 1 wherein X is H, an acyl group, a peptide extension or the acylated form thereof or is a linking group; and
wherein Y is OH, NH$_2$, or a peptide extension or the amidated form thereof or is a linking group.

17. The compound of claim 16 wherein X is H or acyl and Y is OH or NH$_2$.

18. The compound of claim 4 wherein X is H, an acyl group, a peptide extension or the acylated form thereof or is a linking group; and
wherein Y is OH, NH$_2$, or a peptide extension or the amidated form thereof or is a linking group.

19. The compound of claim 18 wherein X is H or acyl and Y is OH or NH$_2$.

20. The compound of claim 1 covalently bound to a solid support.

21. The compound of claim 20 covalently bound to a solid support.

* * * * *